(12) United States Patent
O'Donnell et al.

(10) Patent No.: US 9,198,842 B2
(45) Date of Patent: Dec. 1, 2015

(54) MULTICOMPONENT GLASSES FOR USE IN PERSONAL CARE PRODUCTS

(75) Inventors: Matthew O'Donnell, Leighton Buzzard (GB); Robert Graham Hill, Maidenhead (GB)

(73) Assignee: Repregen Limited, London (GB)

( * ) Notice: Subject to any disclaimer, the term of this patent is extended or adjusted under 35 U.S.C. 154(b) by 441 days.

(21) Appl. No.: 13/381,392

(22) PCT Filed: Jun. 30, 2010
(Under 37 CFR 1.47)

(86) PCT No.: PCT/EP2010/059279
§ 371 (c)(1),
(2), (4) Date: Aug. 17, 2013

(87) PCT Pub. No.: WO2011/000866
PCT Pub. Date: Jan. 6, 2011

(65) Prior Publication Data
US 2014/0056954 A1    Feb. 27, 2014

(30) Foreign Application Priority Data
Jun. 30, 2009    (GB) .................................. 0911365.5

(51) Int. Cl.
| | |
|---|---|
| *A61K 33/08* | (2006.01) |
| *A61K 33/16* | (2006.01) |
| *A61K 33/42* | (2006.01) |
| *A61K 8/19* | (2006.01) |
| *A61K 8/25* | (2006.01) |
| *A61K 8/27* | (2006.01) |
| *A61Q 11/00* | (2006.01) |
| *A61L 27/10* | (2006.01) |
| *C03C 3/062* | (2006.01) |
| *C03C 3/097* | (2006.01) |
| *C03C 3/112* | (2006.01) |
| *C03C 4/00* | (2006.01) |
| *C03C 12/00* | (2006.01) |
| *A61K 8/02* | (2006.01) |
| *A61K 8/21* | (2006.01) |
| *A61K 8/24* | (2006.01) |

(52) U.S. Cl.
CPC . *A61K 8/25* (2013.01); *A61K 8/022* (2013.01); *A61K 8/19* (2013.01); *A61K 8/21* (2013.01); *A61K 8/24* (2013.01); *A61K 8/27* (2013.01); *A61K 33/08* (2013.01); *A61K 33/16* (2013.01); *A61L 27/10* (2013.01); *A61Q 11/00* (2013.01); *C03C 3/062* (2013.01); *C03C 3/097* (2013.01); *C03C 3/112* (2013.01); *C03C 4/0007* (2013.01); *C03C 4/0021* (2013.01); *C03C 4/0035* (2013.01); *C03C 12/00* (2013.01); *A61L 2430/12* (2013.01)

(58) Field of Classification Search
CPC .... A61L 27/10; A61L 2430/12; A61Q 11/00; A61K 8/24; A61K 8/25; A61K 8/19; A61K 33/08; A61K 33/16

USPC ............................................. 424/49, 52, 489
See application file for complete search history.

(56) References Cited

U.S. PATENT DOCUMENTS

| | | |
|---|---|---|
| 3,922,155 A | 11/1975 | Broemer et al. |
| 4,103,002 A | 7/1978 | Hench |
| 4,234,972 A | 11/1980 | Buscemi et al. |
| 4,613,516 A | 9/1986 | Kucheria et al. |
| 4,725,234 A | 2/1988 | Ethridge |
| 5,074,916 A | 12/1991 | Hench |
| 5,120,340 A | 6/1992 | Ducheyne et al. |
| 5,158,934 A | 10/1992 | Ammann et al. |
| 5,290,544 A | 3/1994 | Shimono et al. |
| 5,314,474 A | 5/1994 | Helms et al. |
| 5,480,975 A | 1/1996 | Goldberg et al. |
| 5,645,934 A | 7/1997 | Marcolongo et al. |
| 5,766,611 A | 6/1998 | Shimono et al. |
| 5,856,356 A | 1/1999 | Tsouderos et al. |
| 6,022,819 A | 2/2000 | Panzera et al. |
| 6,054,400 A | 4/2000 | Brink et al. |
| 6,482,444 B1 | 11/2002 | Bellantone et al. |
| 6,569,466 B2 | 5/2003 | Ducheyne et al. |
| 6,773,881 B2 | 8/2004 | Yano et al. |
| 6,905,723 B2 | 6/2005 | Li |
| 2004/0065228 A1 | 4/2004 | Kessler et al. |
| 2004/0162580 A1 | 8/2004 | Hain |
| 2004/0253321 A1 | 12/2004 | Fechner et al. |
| 2005/0054509 A1 | 3/2005 | Hoen et al. |
| 2005/0095303 A1 | 5/2005 | Krenitski et al. |
| 2005/0118236 A1 | 6/2005 | Qiu et al. |
| 2006/0142413 A1 | 6/2006 | Zimmer et al. |
| 2007/0122356 A1 | 5/2007 | Kessler et al. |

FOREIGN PATENT DOCUMENTS

| | | |
|---|---|---|
| EP | 0616814 | 9/1994 |
| EP | 0626165 | 11/1994 |
| EP | 08/02890 | 10/1997 |
| EP | 1481696 | 1/2004 |
| EP | 1405647 | 4/2004 |
| JP | 61205637 | 9/1986 |
| JP | 01-091865 | 4/1989 |
| JP | 2000-143430 | 5/2000 |
| JP | 2005-075724 | 3/2005 |
| WO | 91/17777 | 11/1991 |
| WO | 95/09131 | 4/1995 |
| WO | 95/32709 | 12/1995 |

(Continued)

OTHER PUBLICATIONS

Final Office Action dated May 1, 2014 received in related U.S. Appl. No. 12/304,790.

(Continued)

*Primary Examiner* — Frederick Krass
*Assistant Examiner* — Tracy Liu
(74) *Attorney, Agent, or Firm* — Renner, Otto, Boisselle & Sklar, LLP

(57) ABSTRACT

The present invention relates to multicomponent glasses and their use in powdered form as an additive in personal care products such as toothpastes.

11 Claims, 3 Drawing Sheets

(56) References Cited

FOREIGN PATENT DOCUMENTS

| WO | 96/00536 | 1/1996 |
|---|---|---|
| WO | 98/17236 | 4/1998 |
| WO | 98/40320 | 9/1998 |
| WO | 98/46164 | 10/1998 |
| WO | 00/15167 | 3/2000 |
| WO | 00/16819 | 3/2000 |
| WO | 02/055098 | 7/2002 |
| WO | 02/096391 | 12/2002 |
| WO | 2004/071542 | 8/2004 |
| WO | 2006/050829 | 5/2006 |
| WO | 2007/020613 | 2/2007 |
| WO | 2007083247 | 7/2007 |
| WO | 2007144662 | 12/2007 |
| WO | 2008/090533 | 7/2008 |
| WO | 2008/104964 | 9/2008 |

OTHER PUBLICATIONS

Advisory Action dated Jul. 24, 2014 received in related U.S. Appl. No. 12/304,790.
Non-Final Office Action dated May 13, 2013 received in copending U.S. Appl. No. 12/994,463.
International Preliminary Report on Patentability for PCT/GB2009/001323 (WI PO, Nov. 30, 201 0).
Ananthakunar, S., et al., Gel casting process for Al2O3-SiC nanocomposites and its creep characteristics, Materials Chemistry and Physics,2004;85:151-7.
Barbara, A. et al. Normal matrix mineralization induced by strontium renelate in MC3T3-E1 Osteogenic cells. Metabolism: Clinical and Experimental. (2004) 53(4):532-537.
Buehler, J. et al. Strontium renelate inhibits bone resorption while maintaining bone formation in alveolar bone in monkeys. Bone. (2001) 29(2):76-179.
Buttyan, R., et al., Acute intravesical infusion of a cobalt solution stimulates a hypoxia response, growth and angiogenesis in the rat bladder, J Urol. Jun. 2003;169(6):2402-6.
Chen et al, 45S5 Bioglass®-derived glass-ceramic scaffolds for bone tissue engineering, Biomaterials 27 (2006): 2414-2425.
Christoffersen, J. et al. Effects of strontium ions on growth and dissolution of hydroxyapatite and on bone mineral detection. Bone. (1997) 20(1):47-54.
Delannoy, P. et al. Long term treatment with strontium rene late increases vertebral bone mass without deleterious effects in mice. Metabolism: Clinical and Experimental. (2002) 51 (7):906-911.
Freyman, T. M., et al., Cellular materials as porous scaffolds for tissue engineering, Progress in Materials Science, 2001 ;46:273-282.
Fu, Q., et al., Preparation and bioactive characteristics of a porous 13-93 glass, and fabrication into the articulating surface of a proximal tibia, J Biomed Mater Res A. Jul. 2007;82(1 ):222-229.
Grynpas, M.D. et al. Strontium increases vertebral bone volume in rates at a low dose that does not induce delectable mineralization defect. Bone.(1996) 18(3):253-259.
Harris, E. D., A requirement for copper in angiogenesis, Nutr Rev. 2004, 62(2):60-64.
Hayakawa, S. et al. Biomimetic deposition of calcium phosphates on oxides soaked in simulated body fluid. Journal of Non-Crystalline Solids. (2000) 263-264(1-2):409-415.
Hench & West, The Sol-Gel Process, 90 Chem. Rev. 33 (1989).
Hench, Bioactive Ceramics, in Bioceramics: Material Characteristics Versus In Vivo Behavior (P. Ducheyne & J. E. Lemons, Eds., 1988), 54-71.
Hill, R.G. et al. The influence of strontium-substitution in fluoroapatite glasses and glass-ceramics on nucleation. Journal of Non-crystalline Solids. (2004) 336(3):223-229.
Hill, R.J., An Alternative View of the Degradation of Bioglass, Mal. Sci. Lets. Jul. 1, 1996:15(13):1122-1125.
Jones, J. R., et al., Extracellular matrix formation and mineralization on a phosphate-free porous bioactive glass scaffold using primary human osteoblast (HOB) cells, Biomaterials, 2007, 28:1653-1663.
Jones, J. R., et al., Non-destructive quantitative 3D analysis for the optimisation of tissue scaffolds, Biomaterials. 2007, 28(7):1404-1413.
Jones, J. R., et al., Regeneration of trabecular bone using porous ceramics, Current Opinion in Solid State and Materials Science, 2003;7:301-307.
Kokubo, T., et al., Solutions able to reproduce in vivo surface-structure changes in bioactive glass-ceramic A-W, J Biomed Mater Res. Jun. 1990;24(6):721-734.
Livingston, T., et al., In vivo evaluation of a bioactive scaffold for bone tissue engineering, J Biomed Mater Res. 2002, 62(1):1-13.
Mahmood, J., et al., Geometric effect of matrix upon cell differentiation: BMP-induced osteogenesis using a new bioglass with a feasible structure, J Biochem. 2001, 129(1):163-171.
Martin, F., et al., Copper-dependent activation of hypoxia-inducible factor (HIF)-1: implications for ceruloplasmin regulation, Blood. 2005, 105(12):4613-4619.
Maxwell, P., et al., HIF-1: an oxygen and metal responsive transcription factor, Cancer Bioi Ther. 2004, 3 (1):29-35.
Nielsen, S.P. The biological fole of strontium. Bone. (2004) 35(3):583-588.
Non-Final Office Action dated May 16, 2011 in co-pending U.S. Appl. No. 12/304,790.
Omatete, O., et al., Gelcasting: From Laboratory Development Toward Industrial Production, Journal of the European Ceramic Society, 1997, 17:407-413.
Porter, S., et al., The Adamts Melalloproteinases, Biochemical Journal, 2005, 386(1):15-27.
Rakovan, J. F. et al. Strontium in the Apatite Structure; strontiun fluorapatite and belovite-(Ce). The Canadian Mineralogist. (2000) 38:839-845.
Rokita, E. et al. Bone minerlization after strontium and fluorine treatment in osteoporosis. Nuclear Instruments and Methods in Physics Research B. (1999) 158(1).
Sen, C. K., et al., Copper-induced vascular endothelial growth factor expression and wound healing, Am J Physiol Heart Circ Physiol. 2002, 282(5):H1821-7.
Sepulveda, P., et al., Persulfate-Amine Initiation Systems for Gelcasting of Ceramic Foams, Chern. Mater. 2001, 13, 4065-4070.
Steinbrech, D. S., et al., VEGF expression in an osteoblast-like cell line is regulated by a hypoxia response mechanism, Am J Physiol Cell Physiol. Apr. 2000;278(4):C853-60.
Van Lieshout, T., et al., A hypoxic response induced in MatLyLu cells by cobalt chloride results in an enhanced angiogenic response by the chick chorioallantoic membrane, In! J Oncol. Sep. 2003;23(3):745-50.
Vessillier, S. et al., Latent cy1okines: development of novel cleavage sites and kinetic analysis of their differential sensitivity to MMP-1 and MMP-3, Protein Engineering, Design & Selection: Peds, Dec. 2004;17(12):829-835.
Warren, Clark & Hench, Quality Assurance of Bioactive glass.sup.(R) Powders, 23 J. Biomed. Mal. Res.-App. Biomal. 201 (1989).
Ni et al "Strontium-Containing hydroxyapatite (Sr-HA) Bioactive Cement for primary Hip replacement: An in vivo Study", J. Biomed mater Res Part B: Appl. Biomater 778: 409-415, 2006, Published online Nov. 8, 2005.
Wong et al, "Osteoconduction and Osseointegration of a Strontium-Containing Hydroxyapatite Bioactive Bone Cement: In vitro and In Vivo Investigation", PhD Thesis, The University of Hong Kong; 2004. p. 70-103.
Non-Final Office Action dated Nov. 6, 2013 in co-pending U.S. Appl. No. 12/304,790.

MULTICOMPONENT GLASSES FOR USE IN PERSONAL CARE PRODUCTS

CROSS-REFERENCE TO RELATED APPLICATIONS

This application is the U.S. National Stage filing of International Application Serial No. PCT/EP2010/059279 filed Jun. 30, 2010, which claims priority to GB Application No. 0911365.5 filed Jun. 30, 2009, each of which is incorporated herein by reference in its entirety.

The present invention relates to multicomponent glasses and their use in powdered form as an additive in personal care products such as toothpastes.

A biologically active (or bioactive) material is one which, when implanted into living tissue, induces formation of an interfacial bond between the material and the surrounding tissue. Bioactive glasses are a group of surface-reactive glasses and glass-ceramics designed to induce biological activity that results in the formation of a strong bond between the bioactive glass and living tissue such as bone. The bioactivity of bioactive glass is the result of a series of complex physiochemical reactions on the surface of the glass under physiological conditions, which results in precipitation and crystallisation of a carbonated hydroxyapatite (HCA) phase.

The FDA approved 45S5 Bioglass®, developed by Hench et al. in the 1970s induces HCA formation in vitro and in vivo by a multi-stage dissolution process.

It has been determined that certain multi-component glass compositions show anti-bacterial, biocompatible and bioactive properties rendering them beneficial for use as active ingredients in personal care products such as toothpastes. The glasses of the invention are of the system $SiO_2$—$Na_2O$—$CaO$-$K_2O$—$SrO$—$MgO$—$ZnO$—$P_2O_5$—$B_2O_3$-$MF_x$ (where M is a monovalent or divalent cation and x is 1 or 2). The glasses may comprise at least four components of this system, preferably at least six.

In a first aspect, the invention provides a glass having the composition:
35-55.9 mol % $SiO_2$;
0-30 mol % $Na_2O$;
0-30 mol % $K_2O$;
0-2 mol % ZnO;
0-10 mol % $P_2O_5$, (preferably 2-10 mol %)
0-5 mol % of a metal fluoride; and
a combined mol % of CaO and SrO of 20-30 mol %.

Preferably, the glass has the composition:
35-55.9 mol % $SiO_2$;
9-17 mol % $Na_2O$;
9-20 mol % $K_2O$;
0-2 mol % ZnO;
0-10 mol % $P_2O_5$, (preferably 2-10 mol %)
0-5 mol % of a metal fluoride; and
a combined mol % of CaO and SrO of 20-30 mol %.

Preferably, the glass has the composition:
35-55.9 mol % $SiO_2$;
10-17 mol % $Na_2O$;
10-17 mol % $K_2O$;
0-2 mol % ZnO;
0-10 mol % $P_2O_5$, (preferably 2-10 mol %)
0-5 mol % of a metal fluoride; and
a combined mol % of CaO and SrO of 20-30 mol %.

In an embodiment, the $SiO_2$ content of the glass is 35-50 mol %, preferably 38-47 mol %.

The $Na_2O$ and $K_2O$ content of the glass may each be, independently, 0-30 mol %, 9-30 mol %, 9-25 mol %, 9-20 mol %, 9-17 mol % or 12-15 mol %. In certain embodiments, the mol % content of $Na_2O$ and $K_2O$ is equivalent.

The combined mol % content of CaO+SrO in a glass of the invention may be 21-27 mol. %. For glasses of the invention, the CaO+SrO content may be made up entirely of CaO, entirely SrO or by a combination of CaO and SrO. Preferably, both CaO and SrO are present at a content of at least 1%, preferably at least 2 mol %. In some embodiments, on a molar basis, up to half of the total CaO+SrO content is SrO.

ZnO may be present at 0-1 mol. %.

The $P_2O_5$ content may be at least 2.5 mol %. A content of $P_2O_5$ may be 2.5-10 mol %, preferably 4-10 mol %. The upper limit of $P_2O_5$ in these glasses may be 7 mol %, preferably 6.5 mol %, more preferably 6.33 mol %. The lower limit of $P_2O_5$ in these glasses may be 2.6 mol % or 4 mol %, preferably 4.42 mol %.

The glass composition may include 0-5 mol %, such as 0-4.5 mol %, preferably 0-2 mol %, more preferably 0-1 mol %, of a metal fluoride, for example $CaF_2$.

In some embodiments, at least 0.1 mol %, preferably at least 1 mol % of ZnO and/or a metal fluoride is present.

The glass of the invention may be provided in particulate form, i.e. as a glass powder. The glass powder may have a maximum particle size of 100 microns, preferably 50 microns, more preferably 40 microns. For example, the powder may be obtained by use of a 38 micron sieve accordingly giving a maximum particle size of <38 microns. In certain preferred embodiments, the glass powder has a particle size <10 microns, preferably <5 microns. A preferred particle size range in the glass powder is 1-10 microns, preferably 1-5 microns, more preferably 2-5 microns.

It will be appreciated that the invention encompasses glasses comprising any combination of the composition features set out above.

A glass of the invention is of particular use as an additive in a personal care product. Thus, a personal care product in which a glass of the invention has been included as an additive may be provided. Accordingly, in a second aspect the invention provides a personal care product such as a toothpaste or chewing gum comprising a glass according to the first aspect of the invention. The toothpaste comprises the glass as an additive and may additionally comprise fluoride.

Saliva is saturated with respect to calcium and phosphate and on leaching of ions in the glass (e.g. fluoride, calcium and phosphorus), super-saturation will occur, which can induce precipitation of apatite, repairing the tooth enamel. Glass particles of small enough size can also block the dentinal tubules which when exposed due to enamel loss cause pain. Potassium leached from the glass prevents re-polarisation of the nerve fibre, exposed from lost enamel, which reduces pain and dental sensitivity. Bactericidal ions in the glass such as zinc, when released from the toothpaste, will kill unwanted bacteria reducing conditions such as gingivitis. The inclusion of strontium within the glass composition further enhances the activity of the glass by up-regulating activity of odontoblast cells and enhancing bioactivity.

A glass of the first aspect of the invention or a toothpaste or chewing gum composition of the second aspect of the invention may be provided for use in reducing tooth sensitivity, or treating gingivitis. A glass of the invention may be provided for use as a toothpaste additive.

The invention also provides a method for reducing dental pain and/or dental sensitivity or treating gingivitis comprising administering to a patient in need thereof an effective amount of a glass of the first aspect of the invention or a toothpaste or chewing gum of the second aspect of the invention.

Aluminium is a neurotoxin and inhibitor of in vivo bone mineralisation. The glass of any aspect of the invention may contain trace levels of aluminium or may be aluminium-free.

All preferred features of each of the aspect of the invention apply to all other aspects mutatis mutandis.

The invention may be put into practice in various ways and a number of specific embodiments will be described by way of example to illustrate the invention with reference to the accompanying examples and figures, in which.

Figure 1:
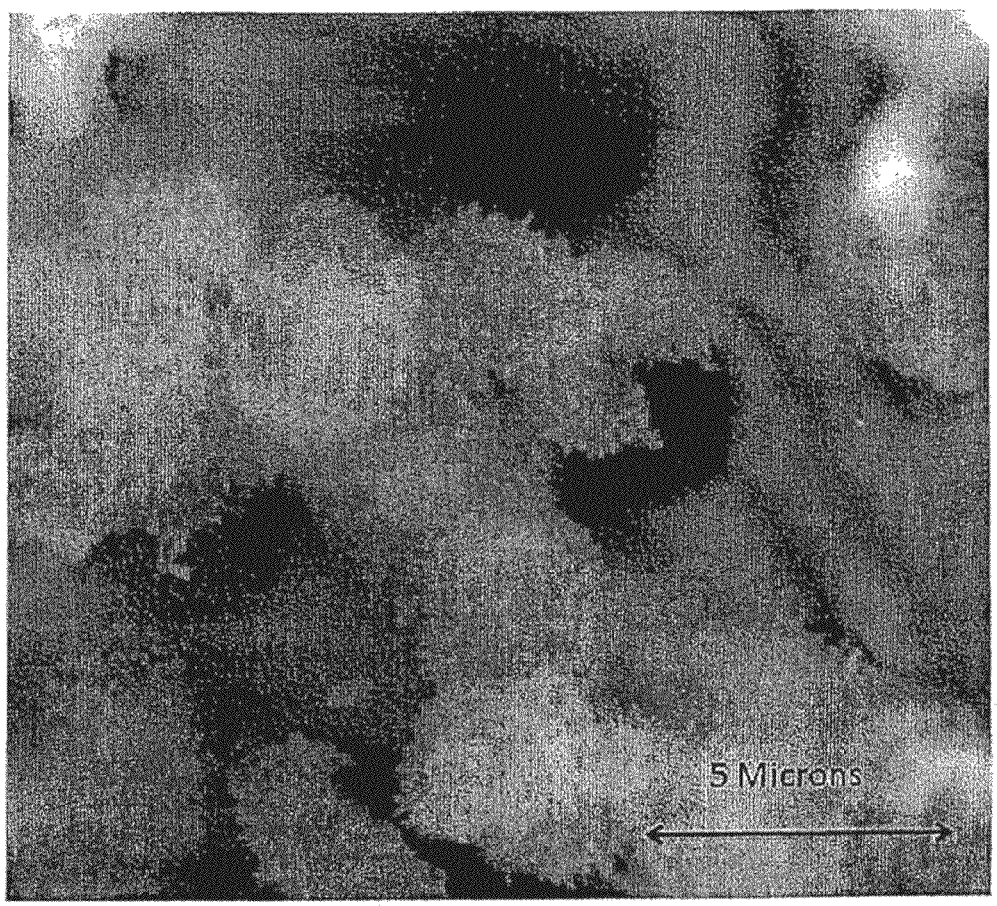
FIG. 1 shows dentinal tubules blocked with apatite precipitation after immersion for 24 hours with HP17 in Tris buffer.

The glasses of all aspects of the present invention may be bioactive glasses. A bioactive glass is one which, when implanted into living tissue, can induce formation of an interfacial bond between the material and the surrounding living tissue. The bioactivity of the glasses of the invention is a result of ion release from the glass composition and, therefore, the glasses of the invention should provide ion release under physiological conditions. Accordingly, glasses of the invention are at least partially resorbable under physiological conditions.

In the context of the present invention, a metal (II) fluoride such as $SrF_2$, $CaF_2$, $ZnF_2$, or $MgF_2$ or a metal (I) fluoride such as KF or NaF.

The terms '45S5' and 'Bioglass®' are interchangeable and refer to the soda-lime-phosphosilicate composition: $46.1SiO_2$-$24.4Na_2O$-$26.9CaO$-$2.6P_2O_5$, in mol. % (45 $SiO_2$-$24.5Na_2O$-$24.5CaO$-$6P_2O_5$, in wt %).

In the context of the invention, and crystalline structure, a 'glass' is an amorphous solid and a 'glass-ceramic' is a glass that, following sintering, has partially crystallised and therefore has a mixed amorphous and crystalline structure.

Throughout the application, where a glass of the invention is described as having or being formed from a composition of certain oxides/fluorides it will be appreciated that the glass composition comprises the oxides/fluorides in the proportions listed, but that other components may be present. However, in each instance where a glass composition is listed the invention also encompasses a glass formed from a composition consisting essentially of the oxides and fluorides listed, i.e. without other components. The components are given on a batch composition basis, i.e. in the proportions in which they are provided in the mixture which is melted to form the glass.

Glass Preparation

Glasses of the invention can be produced by conventional melt-cast techniques. The reagents use to make the glasses may be the oxides of the glass composition and/or other compounds that decompose with heat to form the oxides, for example carbonates. Melt-derived glasses can be prepared by mixing the appropriate carbonates or oxides, melting and homogenising the mixture at temperatures of approximately 1250° C. to 1500° C., cooling the mixture, for example by pouring the molten mixture into water, to produce a glass frit which can be dried, milled and sieved to form a glass powder.

The glasses described in the following examples were prepared by mixing some or all of the reagents $SiO_2$, $Na_2CO_3$, $CaCO_3$, $K_2CO_3$, ZnO, $P_2O_5$, $Ca_3(PO_4)_2$, $NaPO_3$, $Na_3PO_4$ and $MgF_2$ in amounts calculated to give the desired mol % of the various oxides making up the glass composition. Sodium phosphate and calcium triphosphate were preferred as the source of phosphate. It should also be noted that $SrF_2$, $CaF_2$, $ZnF_2$, NaF or KF can be used in place of $MgF_2$. The reagent mixture was melted at 1350-1400° C. in a platinum crucible, frit cast into water, collected in a sieve and then dried for 1 hour at 150° C. The glass frits were milled in a rotary ball mill for 30 min to produce a glass powder and then sieved to produce a glass powder having a maximum particle size of <38 microns. The average particle size was around 20 microns.

As is well recognised in the art, glass compositions are defined in terms of the proportions (mol %) of the oxide (or fluoride) components in the melt mixture from which the glass is formed.

For example, 200 g of glass TP1 can be prepared from 82.99 g $SiO_2$, 38.63 g $Na_2CO_3$, 72.58 g $CaCO_3$, 11.90 g $SrCO_3$, 50.38 g $K_2CO_3$, and 11.07 g $P_2O_5$.

Glass Compositions—Toothpaste Additives

The glass compositions shown in Tables 1A and 1B are particularly useful as an additive for personal care products such as toothpaste.

For the glasses used as an active ingredient in toothpaste, thermal stability less of an issue than for glasses used to form sintered coatings, provided the glass can be melted and quenched without crystallisation. This can be achieved by pouring the melt directly into water. Bioactivity, rate of solubility and particle size and shape are the most important characteristics. The glass solubility can be much higher for this application as the glass is only present in the saliva for a short time. Due to the flexibility of the glass matrix, a number of ions can be incorporated which are beneficial for tooth sensitivity and remineralisation. The silica can act as an abrasive, removing plaque from the tooth surface. Silicon is also known to promote bone health and increase bone mineral density. Potassium and sodium reduce sensitivity by depolarising exposed nerve endings where the enamel has chipped away. Fluorine, calcium, phosphate and strontium will supersaturate the saliva and push the chemical equilibrium towards the precipitation of highly crystalline fluorapatite enamel. Zinc and strontium are bactericidal agents and speed wound healing, reduce infection and kill harmful bacteria in the mouth which cause conditions such as gingivitis. A number of these ions are already present in commercial toothpastes, but as a stoichiometric crystalline compounds (e.g. potassium acetate, strontium chloride, zinc-hydroxyapatite), however the bioactive glasses of this invention allow incorporation of a large number of beneficial ions in a single active ingredient. The glasses of the invention which are of particular use for inclusion as an additive in a toothpaste have a low $SiO_2$ content, preferably 50 mol % or less, which is good for glass solubility. Preferably, they also have high phosphate contents to provide good bioactivity and to buffer pH rises. These glasses also include CaO and SrO at moderate levels and may include $MF_x$ at low levels, all beneficial for apatite formation.

The primary goal of the inclusion of a glass of the invention as an additive in a toothpaste is to provide a reduction in tooth sensitivity with use of the toothpaste. In addition to the effects mentioned above, the primary mechanisms by which sensitivity reduction occurs are physical occlusion of dentinal tubules by glass particles and leaching of Sr ions from the glass.

TABLE 1A (compositions in mol %):

| Oxide | TP1 | TP2 | TP3 | TP4 | TP5 | TP6 | TP7 | TP8 |
|---|---|---|---|---|---|---|---|---|
| SiO$_2$ | 46.13 | 46.13 | 46.13 | 46.13 | 46.13 | 44.47 | 44.47 | 44.47 |
| Na$_2$O | 12.17 | 12.17 | 12.17 | 12.17 | 12.17 | 13.63 | 13.63 | 13.63 |
| CaO | 24.22 | 13.46 | 23.32 | 23.32 | 22.42 | 21.47 | 11.93 | 20.57 |
| SrO | 2.69 | 13.46 | 2.59 | 2.59 | 2.49 | 2.39 | 11.93 | 2.29 |
| K$_2$O | 12.17 | 12.17 | 12.17 | 12.17 | 12.17 | 13.63 | 13.63 | 13.63 |
| CaF$_2$ | 0.00 | 0.00 | 1.00 | 0.00 | 1.00 | 0.00 | 0.00 | 1.00 |
| ZnO | 0.00 | 0.00 | 0.00 | 1.00 | 1.00 | 0.00 | 0.00 | 0.00 |
| P$_2$O$_5$ | 2.60 | 2.60 | 2.60 | 2.60 | 2.60 | 4.42 | 4.42 | 4.42 |

| Oxide | TP9 | TP10 | TP11 | TP12 | TP13 | TP14 | TP15 | TP16 | TP17 | TP18 |
|---|---|---|---|---|---|---|---|---|---|---|
| SiO$_2$ | 44.47 | 44.47 | 38.14 | 38.14 | 38.14 | 38.14 | 38.14 | 44.00 | 37.75 | 36.41 |
| Na$_2$O | 13.63 | 13.63 | 14.81 | 14.81 | 14.81 | 14.81 | 14.81 | 10.00 | 14.66 | 28.28 |
| CaO | 20.57 | 19.67 | 23.32 | 12.96 | 22.42 | 22.42 | 21.52 | 15.00 | 25.65 | 24.74 |
| SrO | 2.29 | 2.19 | 2.59 | 12.96 | 2.49 | 2.49 | 2.39 | 15.00 | 0.00 | 0.00 |
| K$_2$O | 13.63 | 13.63 | 14.81 | 14.81 | 14.81 | 14.81 | 14.81 | 10.00 | 14.66 | 0.00 |
| CaF$_2$ | 0.00 | 1.00 | 0.00 | 0.00 | 1.00 | 0.00 | 1.00 | 0.00 | 1.00 | 4.53 |
| ZnO | 1.00 | 1.00 | 0.00 | 0.00 | 0.00 | 1.00 | 1.00 | 1.00 | 0.00 | 0.00 |
| P$_2$O$_5$ | 4.42 | 4.42 | 6.33 | 6.33 | 6.33 | 6.33 | 6.33 | 5.00 | 6.27 | 6.04 |

TABLE 1B (compositions in wt %):

| Oxide | TP1 | TP2 | TP3 | TP4 | TP5 | TP6 | TP7 | TP8 |
|---|---|---|---|---|---|---|---|---|
| SiO$_2$ | 41.50 | 38.54 | 41.39 | 41.37 | 41.26 | 38.84 | 36.44 | 38.75 |
| Na$_2$O | 11.30 | 10.49 | 11.27 | 11.26 | 11.23 | 12.28 | 11.52 | 12.25 |
| CaO | 20.33 | 10.49 | 19.53 | 19.52 | 18.72 | 17.50 | 9.12 | 16.72 |
| SrO | 4.17 | 19.39 | 4.01 | 4.01 | 3.84 | 3.59 | 16.85 | 3.43 |
| K$_2$O | 17.17 | 15.95 | 17.12 | 17.12 | 17.07 | 18.66 | 17.51 | 18.62 |
| CaF$_2$ | 0.00 | 0.00 | 1.17 | 0.00 | 1.16 | 0.00 | 0.00 | 1.13 |
| ZnO | 0.00 | 0.00 | 0.00 | 1.21 | 1.21 | 0.00 | 0.00 | 0.00 |
| P$_2$O$_5$ | 5.53 | 5.14 | 5.52 | 5.52 | 5.50 | 9.12 | 8.56 | 9.10 |
| Total | 100.00 | 100.00 | 100.00 | 100.00 | 100.00 | 100.00 | 100.00 | 100.00 |

| Oxide | TP9 | TP10 | TP11 | TP12 | TP13 | TP14 | TP15 | TP16 |
|---|---|---|---|---|---|---|---|---|
| SiO$_2$ | 38.73 | 38.63 | 32.37 | 30.26 | 32.29 | 32.28 | 32.20 | 35.76 |
| Na$_2$O | 12.24 | 12.21 | 12.97 | 12.12 | 12.93 | 12.93 | 12.90 | 8.38 |
| CaO | 16.71 | 15.94 | 18.47 | 9.59 | 17.72 | 17.71 | 16.96 | 11.38 |
| SrO | 3.43 | 3.27 | 3.79 | 17.73 | 3.64 | 3.64 | 3.48 | 21.03 |
| K$_2$O | 18.61 | 18.56 | 19.71 | 18.42 | 19.66 | 19.65 | 19.60 | 12.74 |
| CaF$_2$ | 0.00 | 1.13 | 0.00 | 0.00 | 1.10 | 0.00 | 1.10 | 0.00 |
| ZnO | 1.18 | 1.18 | 0.00 | 0.00 | 0.00 | 1.15 | 1.14 | 1.10 |
| P$_2$O$_5$ | 9.09 | 9.07 | 12.69 | 11.87 | 12.66 | 12.66 | 12.62 | 9.60 |
| Total | 100.00 | 100.00 | 100.00 | 100.00 | 100.00 | 100.00 | 100.00 | 100.00 |

By virtue of one or more of the bioactive, anti-microbial, anti-inflammatory, hygroscopic, anti-fungal and abrasive properties provided by glasses of the invention, the glasses of the present invention can be used as an additive in a variety of personal care products including, but not limited to: toothpaste and mouthwash; sun care products, in which the glass provides enhanced UV protection; diaper, baby wipe and hand wipe, baby powder and body powder and diaper rash products; cosmetic products, including makeup products; tampon, sanitary towel and pantiliner products; acne prevention and treatment compositions; facial cleansing, toning and exfoliating products and makeup removal products; skin moisturizing products such as facial moisturizing, anti-wrinkle, eye treatment, hand lotion and body lotion products; foot care products such as products for the treatment of foot odour, althlete's foot and other fungal infections; anti-itch products; anti-bacterial, antiseptic, antibiotic and first aid products such as wound dressings; cleaning products such as bath and shower soap in bar, liquid and gel form and bath salt products; hair care products such as shampoo, hair conditioning and hair detangling products; hair mousse, hair gel and hair spray; antiperspirant and deodorant products in powder, cream, roll-on, aerosol and stick form; aftershave and shaving products such gel, cream, powder, soap or lotion shaving products; nursing pads for bras; depilatory, epilatory and hair bleaching products in cream, wax and powder forms; wig and toupee powder products; shoulder pads; freckle coating products, eye drops; and contact lens treatment products.

A toothpaste comprising a glass can have the following components in addition to the glass additive: glycerine, sodium, lauryl sulphate, PEG, carbomer, potassium acesulfame, titanium dioxide, silica and triethanolamine.

Measurement of Bioactivity

The rate of development of a hydroxycarbonated apatite (HCA) layer on the surface of glass exposed to simulated body fluid (SBF) provides an in vitro index of bioactivity. In the context of the present invention, a glass is considered to be bioactive if, on exposure to SBF in accordance with the following procedure, deposition of a crystalline HCA layer occurs. Following this procedure for glass HP2, HCA formation was seen in vitro in 2 weeks, which is comparable to Bioglass®.

Preparation of Simulated Body Fluid (SBF)

The preparation of SBF was carried out according to the method of Kokubo and Takadama, Biomaterials 27 (2006): 2907-2915 with one liter of SBF containing the following reagents dissolved in distilled water:

| Order | Reagent | Amount |
|---|---|---|
| 1 | NaCl | 8.035 g |
| 2 | NaHCO$_3$ | 0.355 g |
| 3 | KCl | 0.225 g |
| 4 | K$_2$HPO$_4$•3H$_2$O | 0.231 g |
| 5 | MgCl$_2$•6H$_2$O | 0.311 g |
| 6 | 1.0m-HCl | 39 ml |
| 7 | CaCl$_2$ | 0.292 g |
| 8 | Na$_2$SO$_4$ | 0.072 g |
| 9 | Tris | 6.118 g |
| 10 | 1.0m-HCl | 0-5 ml |

Assay to Determine Bioactivity:

Glass powders were analysed using the standard (ISO23317) simulated body fluid (SBF) test to determine in vitro apatite forming ability, an indicator of in vivo behaviour. In the analysis, glass powder was used rather than a solid disk specimen. The amount of glass powder used was calculated to give a surface area ratio of the powder to the SBF volume corresponding to the ratio given in the standard, which was 67.5 mg of 225 micron diameter glass powder to 60 ml of SBF.

The formation of HCA can be measured by micro-Raman spectroscopy. After soaking in SBF for 1 day, 1 week, 2 weeks, 3 weeks and 4 weeks, the dried powders were analysed using micro-Raman spectroscopy to observe the development of the characteristic HCA phosphate $v_1$ vibrational band at around 960 cm$^{-1}$.

Assessment of Tooth Sensitivity

Private trials carried out with glasses of the invention have demonstrated that a toothpaste including glass TP2 as an additive is successful in reducing tooth sensitivity. The toothpaste composition was:

| | Conc. Range |
|---|---|
| Glycerin | over 30% |
| Sodium Lauryl Sulfate | 1-5% |
| Carbomer (benzene free) | less than 1% |
| Postassium Acesulfame | less than 1% |
| Titanium Dioxide | less than 1% |
| Silica | 15-30% |
| Glass | 5-15% |
| Triethanolamine | less than 1% |
| PEG-8 | 1-5% |

This toothpaste formulation was provided, without identification of the composition of the TP2 additive, to trial subjects with sensitive teeth to use instead of their normal toothpaste over a two-week trial period. All of the trial subjects had previously been using sensitivity-reducing toothpastes. Over 80% of the subjects reported a reduction in tooth sensitivity by the end of the two-week trial, with almost two-thirds reporting a sensitivity reduction within one week. Subjects were asked whether their sensitivity related to one or more of four specific triggers: hot, cold, sweet and sour. Reductions in sensitivity were reported for all triggers, with the greatest reductions seen for the hot and sour triggers. This can be attributed to increased Sr leaching in hot fluid and the creation of a mildly alkaline environment by the presence of glass thereby neutralising the acidic cause of a sour sensitivity.

Apatite Formation in Tris Buffer pH 7.5

Apatite formation was investigated in Tris buffer pH 7.5 using TP17 and TP18. The test conditions used were:
75 mg of <45 micron glass
50 ml Tris buffer pH 7.5
Temperature: 37° C.

The 45S5 Bioglass does not form apatite under these test conditions.

An XRD pattern obtained with TP17 showed the formation of glass apatite peaks at approximately 26 and 32 Two Theta) (°), each with an intensity of approximately 2600 CPS.

Figure 2:
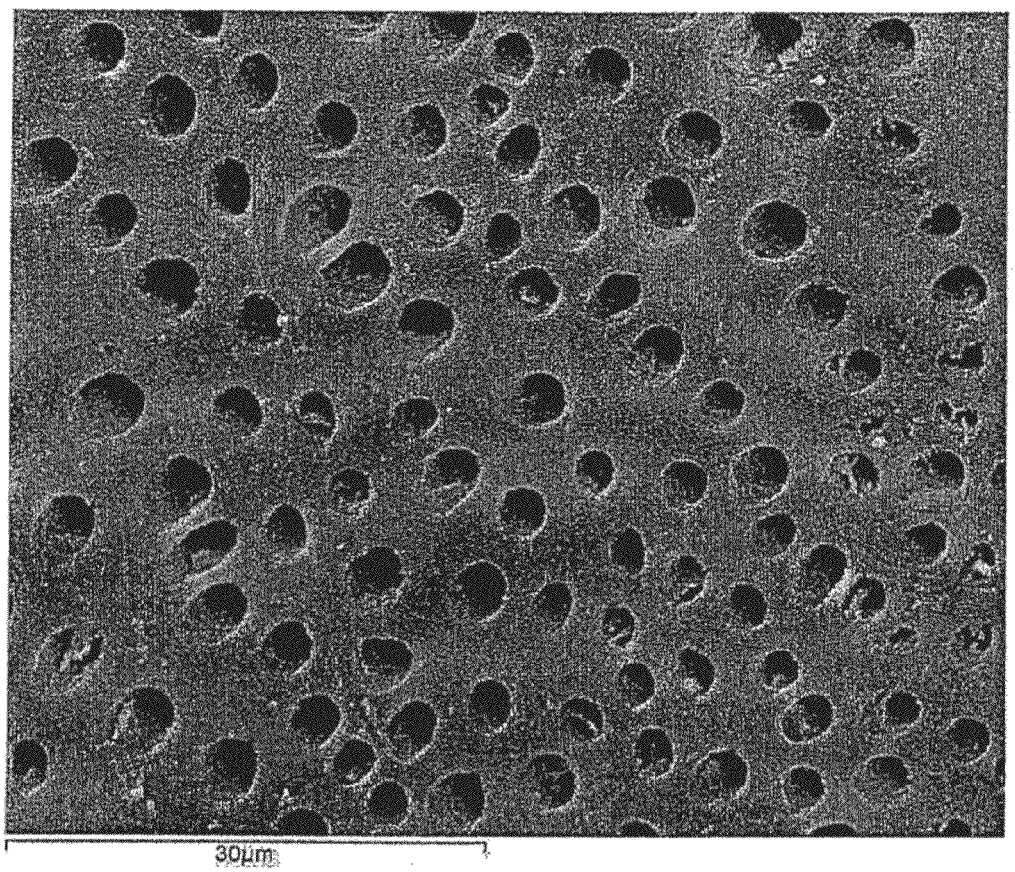
FIG. 2 shows control dentine etched with citric acid for 30 seconds.

Immersion of dentinal tubules with TP17 in Tris buffer resulted in the blocking of the dental tubules with precipitated apatite (see FIG. 1). FIG. 2 shows dental tubules produced in control dentine by etching with citric acid for 30 seconds.

Figure 3:
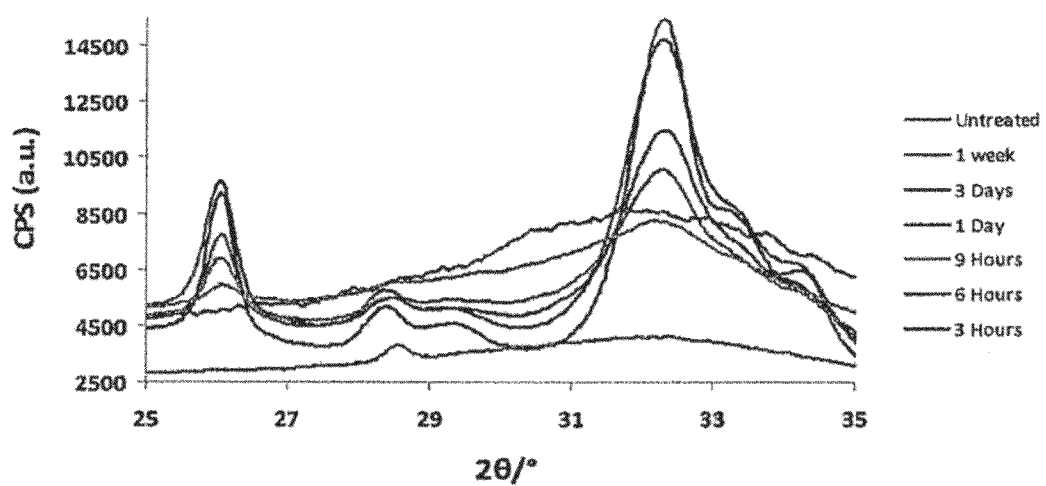
FIG. 3 shows XRD patterns for HP18 after immersion in Tris buffer at pH 7.25.

XRD patterns obtained after immersion of TP18 in Tris buffer at pH 7.25 showed the formation of apatite from six hours (see FIG. 3). The intensity of the peak at approximately 32 Two Theta)(°) increases with the increasing time periods of 9 hours, 1 day, 3 days and 1 week. The untreated sample does not show a peak at approximately 26 and 32 Two Theta) (°).

The invention claimed is:

1. A bioactive glass having the composition:
38-47 mol % SiO$_2$;
9-30 mol % Na$_2$O;
0-30 mol % K$_2$O;
0-2 mol % ZnO;
2.5-10 mol % P$_2$O$_5$;
1-5 mol % of a metal fluoride; and
a combined mol % of CaO and SrO of 20-30 mol %.

2. The glass of claim 1 having the composition:
38-47 mol % SiO$_2$;
9-17 mol % Na$_2$O;
9-20 mol % K$_2$O;
0-2 mol % ZnO;
2.5-10 mol % P$_2$O$_5$;
1-5 mol % of a metal fluoride; and
a combined mol % of CaO and SrO of 20-30 mol %.

3. The glass of claim 1, wherein the glass has the composition:
38-47 mol % SiO$_2$;
10-17 mol % Na$_2$O;
10-17 mol % K$_2$O;
0-2 mol % ZnO;
2.5-10 mol % P$_2$O$_5$;
1-5 mol % of a metal fluoride; and
a combined mol % of CaO and SrO of 20-30 mol %.

4. The glass of claim 1, wherein the glass comprises one, more than one or all of:
a) an Na$_2$O and K$_2$O content each, independently, of 12-15 mol %;
b) a combined mol % content of CaO+SrO of 21-27 mol %;
c) a ZnO content of 0-1 mol %; and
d) 1-2 mol % of a metal fluoride.

5. The glass of claim 1 comprising at least 0.1 mol % ZnO and/or a metal (II) fluoride.

6. The glass of claim 1, wherein the glass is aluminium free.

7. The glass of claim 1 provided in particulate form.

8. The glass of claim 7, having maximum particle size of 100 microns.

9. A personal care product comprising a glass of claim 1.

10. A toothpaste or chewing gum comprising a glass of claim 1.

11. A method for reducing dental pain and/or dental sensitivity or treating gingivitis comprising administering to a patient in need thereof an effective amount of a glass of claim 1.

* * * * *